United States Patent [19]

Mohajer

[11] Patent Number: 5,632,959
[45] Date of Patent: May 27, 1997

[54] COMBINATION HOLDER FOR SPECIMEN SLIDE

[76] Inventor: Reza S. Mohajer, 1565 W. Big Beaver Rd., Building F, Troy, Mich. 48084

[21] Appl. No.: 514,557

[22] Filed: Aug. 14, 1995

[51] Int. Cl.$^6$ .............................. B01L 9/00; B65D 85/48
[52] U.S. Cl. ........................ 422/104; 427/2.11; 206/456
[58] Field of Search .................... 427/2.11; 422/102, 422/104; 206/508, 509, 454, 456; 211/88, 89, 104; 118/52

[56] References Cited

U.S. PATENT DOCUMENTS

| | | | |
|---|---|---|---|
| 4,031,852 | 6/1977 | Clarke et al. | 118/52 |
| 4,103,643 | 8/1978 | Staunton | 118/52 |
| 4,108,109 | 8/1978 | Barger et al. | 118/52 |
| 4,589,551 | 5/1986 | Hellon | 206/456 |
| 4,753,349 | 6/1988 | Monek | 206/456 |
| 4,777,020 | 10/1988 | Brigati | 422/99 |
| 4,801,431 | 1/1989 | Cuomo et al. | 422/104 |
| 5,292,000 | 3/1994 | Levy | 206/456 |
| 5,326,398 | 7/1994 | Kelley et al. | 118/52 |
| 5,370,128 | 12/1994 | Wainwright | 128/756 |

*Primary Examiner*—Diana Dudash
*Attorney, Agent, or Firm*—Marc J. Luddy

[57] ABSTRACT

A holder for a slide comprising: a base, sized to accommodate the slide on a portion of its area and having an integrated hinge that permits the base to fold over itself and thereby cover the slide; at least three retaining clips affixed to the base and positioned to contact the slide and hold the slide against the base, the at least three retaining clips sized to maintain the portion of the base that covers the slide at a uniform distance from the slide; a tab formed as part of the base and positioned adjacent to the at least three retaining clips; and a clasp positioned on the base to keep the base folded over itself.

10 Claims, 2 Drawing Sheets

COMBINATION HOLDER FOR SPECIMEN SLIDE

BACKGROUND OF THE INVENTION

The present invention relates to an improved holder for a specimen slide. Most specifically, the present invention involves an improved holder that securely holds a microscope slide so that scrapings collected using a CELLSWEEP® (the construction of which is described in detail in U.S. Pat. Nos. 5,002,408 11 Jun. 1991; DES 335,706 18 May 1993; and 5,279,307 18 Jan. 1994 to Mohajer) cervical sampling swab can be transferred swiftly and easily on to the slide without touching the slide. The slide holder of the present invention is configured so that can be closed immediately to protect the smear on the slide as it dries.

FIELD OF THE INVENTION

The number of diagnostic medical procedures performed increases every year. This is due to the fact that medical science can identify more disease conditions, more rapidly using ever smaller amounts of material. Another reason is the increase of antibiotic resistance necessitates accurate identification of a disease organism so that an appropriate antibiotic can be chosen. Finally, medical science is now able to cure previously fatal diseases it they can be identified at their early stages.

Many modern diagnostic procedures involve putting a sample on a slide and examining it under a microscope. Blood, sputum, stool, urine, as well as cell scrapings from inside or outside of the body are routinely "smeared" on a specimen slide for microscopic examination. (As used herein, "slide" refers to all types of relatively thin pieces of material, typically light transmitting, used as a specimen holder. The most common such slide being the ubiquitous 2×6 cm, clear glass, "microscope slide").

Once the sample has been smeared on a slide it is typically allowed to dry and additionally fixed or stained before being examined. The examination of such samples, in order to take advantage of economies of scale, is now done routinely at a centralized laboratory.

A number of mailers and holders have been developed to transport slides to an examination location. For example:

U.S. Pat. No. 4,078,656 to Crane, et al., 14 Mar. 1978, describes a paper or cardboard package for containing and delivering a slide. The package comprises two side panels joined by a narrow end wall, with end walls at the remote ends of the panels, edge wall, and side flaps. A slide is fastened removably in the package with various paper flaps and adhesive spots, along with a removable sampling device such as a spatula or a tongue depressor. The slide and sampling device are removed, and a specimen taken and smeared on the slide. The slide is then replaced in the holder, which is folded around the slide.

U.S. Pat. No. 4,819,804 to Levy, 11 Apr. 1989, describes a package for transporting a glass slide constructed for example out of a light weight material like styrofoam. A thin base sheet of the material is provided with a rectangular recess slightly smaller than the slide and the slide is pressed into this recess. Three edges of the base are each provided with a ridge leaving the fourth edge clear and a thin cover sheet of the same styrofoam material fits snugly within the ridges where it is yieldably held in position covering the slide.

U.S. Pat. No. 4,976,354 to Levy, 11 Dec. 1990, describes a package for biological specimen slides made of an elongated sheet divided by a transverse crease line into a cover portion and a base portion. A tab at one end engages a slot near the opposite end for keeping the sheet folded along the crease line to cover a slide held between the base and cover by two slide retainers on the base portion. The cover is longer than the base and arches away from contact with the biological specimen on the slide.

U.S. Pat. No. 5,044,500 to Weber, et al., 3 Sep. 1991, describes a container for handling and transporting glass slides. This container comprises a base support having at least one slide retention well for receiving a single slide and a cover for engagement with the base support. A projection is provided on the cover for allowing alternating access to different portions of the slide as desired.

U.S. Pat. No. 5,050,735 to Levy 24 Sep. 1991, describes a specimen kit for smear specimens comprising collection swabs and a slide holder that together form a long flat package. Perforation lines on the flat package make it possible to separate the long flat package into a shorter package for the slide. This shorter package has one end panel containing a slot or tab configuration for holding the slide.

U.S. Pat. No. 5,090,568 to Tse, 25 Feb. 1992 describes a slide mailer formed of one piece of molded, resilient polymeric material comprising a base, a cover, and a living hinge section. The base and cover pivot about the hinge section and snap fit together at two areas to retain the slide in the mailer between various protrusions molded into the walls, base, and cover of the mailer.

These prior art devices all have a variety of drawbacks.

For example, the devices described in U.S. Pat. Nos. 4,078,656; 4,976,354; 5,050,735 are little more than paper folders for holding a specimen slide. The slide is held in place with folds and flaps and generally requires a spot of adhesive to assure that it does not slide out when the holder is handled. This adhesive often holds too well and the effort needed to lever the slide away from the holder sometimes results in a broken slide. Once the slide is removed from the holder, it often still has adhesive on it which must be removed as a separate step. In addition, many of these holders require the user to rip off portions of paper and perform a variety of folding operations to "assemble" the finished holder.

The inventions described in U.S. Pat. Nos. 4,819,804; 5,044,500; 5,090,568 describe the use of a resilient material. These patents appear directed primarily to finding a design that can be manufactured with the minimum number of steps because they teach simultaneously forming various protrusion and wells for holding the slide at the same time as the holder itself is formed.

No prior art device has considered that in addition to transporting the slide, it is necessary to process and handle it as well.

SUMMARY OF THE INVENTION

An object of the present invention is a holder for a specimen slide that protects the slide during transport.

Another object of the invention is a holder for a slide that permits easy processing of the slide once the sample has been transferred to it.

These and other objects of the invention are satisfied by a holder for a slide comprising: a base, sized to accommodate the slide on a portion of its area and having an integrated hinge that permits the base to fold over itself and thereby cover the slide; at least three retaining clips affixed to the base and positioned to contact the slide and hold the slide against the base, the at least three retaining clips sized to maintain the portion of the base that covers the slide at a uniform distance from the slide; a tab formed as part of said base and positioned adjacent to the at least three retaining clips; and a clasp positioned on said base to keep the base folded over itself.

Another object of the present invention is a method for preparing a specimen slide using a slide holder comprising: a base, sized to accommodate the slide on a portion of its area and having an integrated hinge that permits the base to fold over itself and thereby cover the slide; at least three retaining clips affixed to the base and positioned to contact the slide and hold the slide against the base, the at least three retaining clips sized to maintain the portion of the base that covers the slide at a uniform distance from the slide; a tab formed as part of the base and positioned adjacent to the at least three retaining clips; retaining posts positioned to keep the slide positioned underneath the at least three clips; a sampling device held in place against the base; and a clasp positioned on the base to keep the base folded over itself; the method comprising the steps of: removing the sampling device from the base and obtaining a sample on it; holding the base in position by pressing on the tab with a finger of the opposite hand; moving the sampling device to transfer the sample onto the slide; closing the holder by folding the base along the hinge; and engaging the clasp to keep the holder closed.

Still another object of the invention is a holder for a slide comprising: a base, sized to accommodate the slide on a portion of its area and having an integrated hinge that permits the base to fold over itself and thereby form a cover over the slide; at least three retaining clips affixed to the base and positioned to contact the slide and hold the slide against the base, the at least three retaining clips sized to maintain the portion of the base that covers the slide at a uniform distance from the slide; at least one retaining post positioned to keep the slide positioned underneath the at least three clips; a tab for handling the holder, this tab formed as part of the base and positioned adjacent to the at least three retaining clips; and a clasp positioned on the base to keep the cover folded and covering the slide.

BRIEF DESCRIPTION OF THE DRAWINGS

The same reference numbers are used to refer to corresponding parts in each of the drawings.

DETAILED DESCRIPTION OF THE INVENTION

Unlike the prior art, the present invention describes a slide holder having fitted clips and retaining posts as well as an integrated tab for easy immobilization of the holder. These clips, posts, and tab make it extremely simple to insert and remove a slide into the holder. In addition, the clips hold the slide firmly in place without the necessity of adhesive dots or the like. Further, when the case is closed, the cover is prevented from coming in contact with the surface of the slide. This makes it possible to close the cover of the slide holder before the surface of the slide is dried. In addition, closing the cover prevents contaminants from coming into to contact with the wet slide and diluting or reducing the amount of the sample.

A particularly unique feature of the present invention is the integrated handling tab. Not only does the tab permit a user to easily immobilize the holder on the bench top, it also permits the slide to be removed from the holder with one hand. The tab is formed as part of the base opposite the retaining clips. By grasping the holder between the thumb and the forefinger with the thumb up, it's a simple motion to slide the thumb until it contacts the edge of the slide and by applying gentle lateral pressure, to push the slide out of the retaining clips.

The ease with which a slide can be removed from the present invention represents a major improvement over the prior art. The prior art holders almost uniformly require digging and prying with the finger nails to free the slide from folds and adhesives or integrated retaining wells. This requires the application of considerable force which makes breaking a slide or getting cut by the edge of a slide a real possibility and increases the chance of self inoculation with a hazardous organism or cancerous cells. This hazard is entirely avoided through the use of the present invention.

Figure 1:
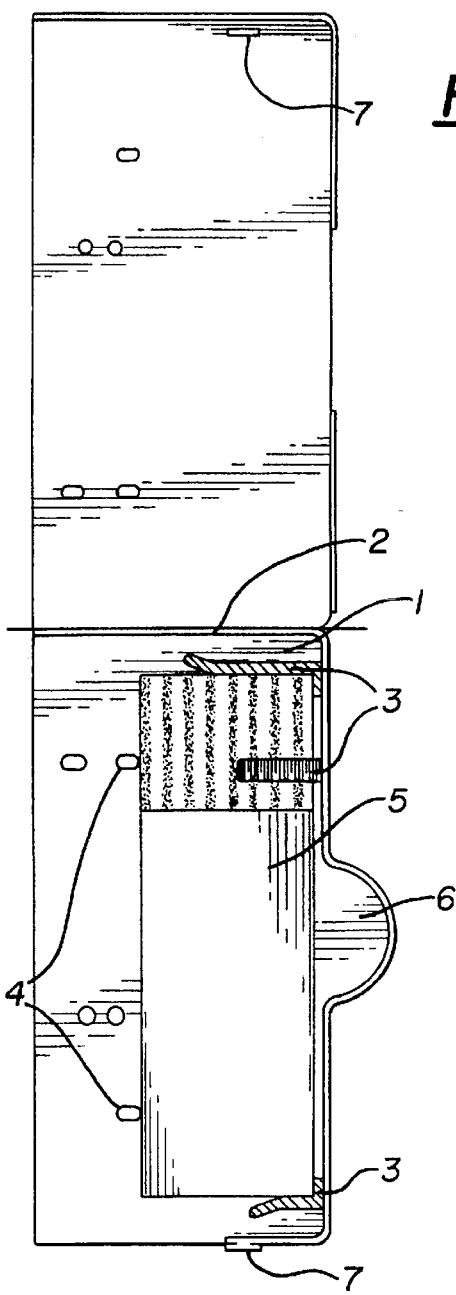
FIG. 1 shows a top view of an embodiment of the present invention with a slide in place.
Figure 5:
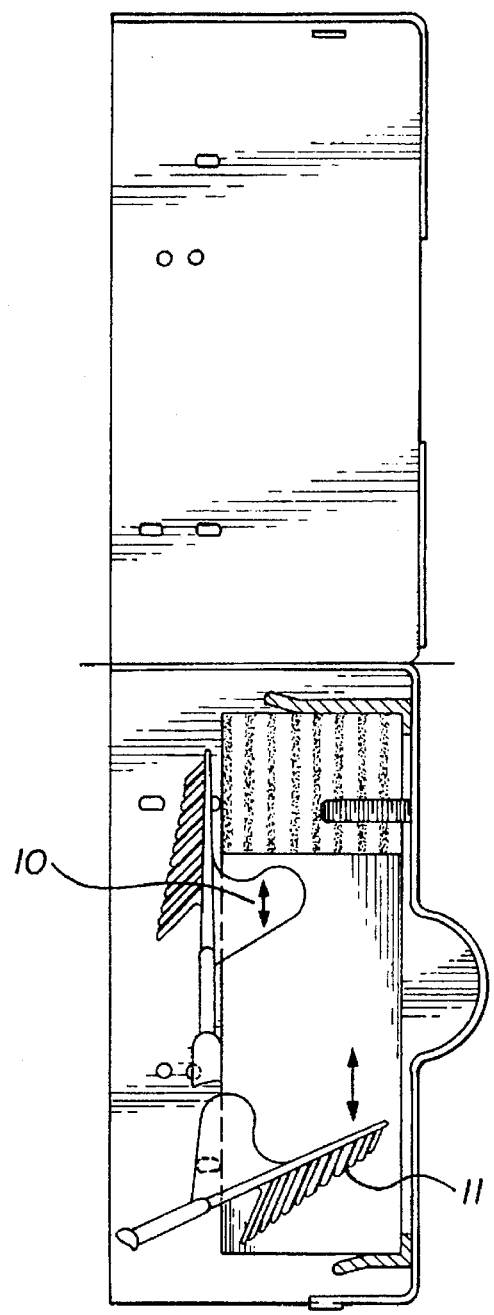
FIG. 5 shows the method of transferring sampled cell material using a CELLSWEEP® onto an embodiment of the present invention.

FIG. 1 shows a top view of an embodiment of the present invention with a slide in place. This embodiment is illustrated as holding a standard rectangular microscope slide, however, slides of different shapes are specifically included in the invention. In this embodiment, the holder comprises a base 1 formed out of any rigid material. Preferably, the material is a clear thermoplastic such as polyethylene or polycarbonate. A rectangular slide 5 is held in place by retaining clips 3. In this illustration, the slide has an identification area at one end and is held in place by a first clip positioned on one distal edge, a second clip positioned on the distal edge opposite the first clip, and a third clip positioned over the identification area of the slide. In addition, retaining posts 4 are positioned to prevent the slide from coming out from underneath of the clips 3. Because the material of the holder is clear, the identifying information written on the slide can be read through the holder thus eliminating the necessity of rewriting the same identifying information on the holder itself. A hinge 2 permits the holder to be closed over the slide. The integrated tab 6 permits easy immobilization of the slide holder when the slide is being inserted or removed into the holder or when a specimen is being transferred from a collection devices onto a slide positioned in the holder (as shown in FIG. 5). In addition, the integrated tab permits easy removal of the slide holder from its shipping package and easy removal of the slide from the holder. An integrated clasp 7 keeps the base 1 folded over itself.

Figure 2:
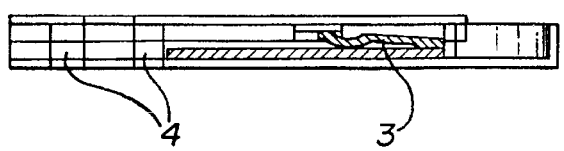
FIG. 2 shows a cross sectional view of the embodiment of FIG. 1 with a slide in place and the base folded over itself to form a protective cover for the slide.
Figure 3:
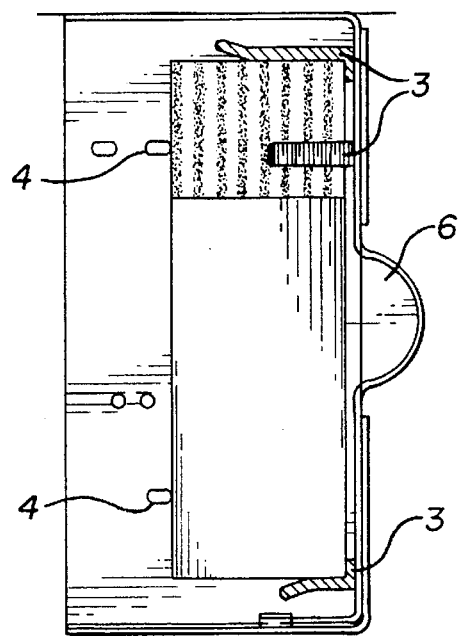
FIG. 3 shows a cross sectional view of the embodiment of FIG. 1 with a slide in place and the base folded over itself to form a protective cover for the slide.

FIG. 2 shows a cross sectional view and FIG. 3 shows a top view of the embodiment of FIG. 1 with the base folded along the hinge 2. FIG. 2 specifically shows how the clips 3 and posts 4 serve as spacers to hold the portion of the base 1 that folds over the slide along the hinge 2 from coming into contact with the surface of the slide. This feature permits the holder to be closed on a slide immediately after a specimen has been transferred to the slide. It also permits closing the holder immediately after a fixative or stain has been applied.

The fact that the slide holder of the present invention can be closed on a wet slide is an enormous timesaver in a busy doctor's office or clinic. Once the specimen has been transferred, the slide holder can be closed and placed out of the way to dry without the necessity of having to constantly check to see if the slide is dried before closing it as required by much of the prior art. In addition, contamination of the slide by any extraneous particles while the holder is open to the air as well as the loss of specimen material that occurs if a prior art holder is closed on top of a wet slide is avoided.

The integrated tab 6 simplifies the insertion and removal of the slide as well as the transfer of the specimen to the slide. In use, one merely immobilizes the slide holder on a table or bench top by pressing on the tab 6 with a finger of one hand while simultaneously transferring the specimen to the slide or removing the slide from the holder.

The integrated clasp 7 makes it possible to open and reclose the slide holder of the present invention with ease. This feature together with the ability to close the slide holder on a wet slide simplifies processing of the specimen. For example, a number of specimens can be taken successively and each one transferred to a slide contained in the slide holder of the present invention. As each specimen is transferred, the slide holder is immediately closed around the slide and the holders stacked. The stacked holders can then be transferred to a laboratory area for further processing. In the laboratory area, each holder can be opened in turn and without having to remove the slide from the holder the specimen treated with fixative or diagnostic stain. The slide holder can then be reclosed immediately until such time as the slide is examined.

Figure 4:
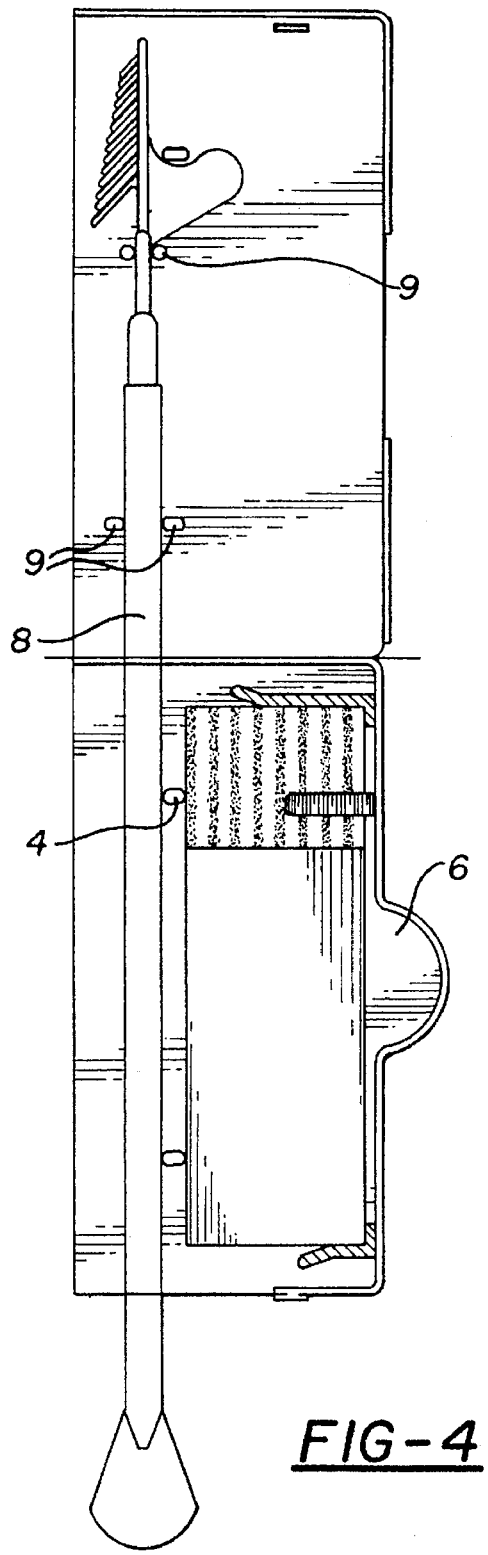
FIG. 4 shows an embodiment of the invention with a Cell-Sweep® in place.

FIG. 4 shows an embodiment of the invention with a CELLSWEEP® in place. (The CELLSWEEP® is described in detail in U.S. Pat. Nos. 5,002,408 11 Jun. 1991; DES 335,706 18 May 1993; and 5,279,307 18 Jan. 1994 to Mohajer.) Briefly it is a unique sampling tool for simultaneously gathering endo-cervical and exo-cervical cells for examination. In this embodiment of the invention, the retaining posts 4 and additional retaining posts 9 hold an open slide holder with a slide and a CELLSWEEP®. Multiple holders with attached CELLSWEEP® are packaged vertically in a carton, like cards in a filing cabinet, with the tab 6 extending upright like an index tab. In use, one merely pulls the holder/CELLSWEEP® combination from the carton by grasping the tab 6 between the thumb and index finger.

FIG. 5 shows how the embodiment of FIG. 4 is configured specifically to simplify the one step transfer of exo- and endo-cervical cells from the CELLSWEEP® unto the slide. After swabbing the cervix using a CELLSWEEP®, exo-cervical cells are on the tab 10 and endocervical cells are on the comb 11. Transfer is effected by anchoring the holder to the bench top by pressing on the tab 6 with a finger while simultaneously moving the CELLSWEEP® parallel to the longitudinal edge of the slide so that the cells on the tab 10 are transferred in a longitudinal stripe that has a width less than half of the width of the slide along the edge of the slide opposite the tab 6. The CELLSWEEP® is then rolled between the fingers so that the comb 11 will come into contact with the slide, and the CELLSWEEP® moved parallel to the longitudinal edge of the slide closest to the tab 6 so that the cells on the comb 11 are transferred in a longitudinal stripe that has a width less than half of the width of the slide along the edge of the slide opposite the tab 6.

One skilled in the art can visualize a number of variations of the configurations described above that are within the scope of the present invention. For example, rather than standard rectangular slides the present invention could be configured to hold custom slides of any shape.

For specific sampling purposes that might produce unusually wet slides or require specific fixative or stains as a matter of routine, the holder of the present invention could be formed to have openings or perforations specifically sized for rapid drying, fixing, or staining of the specimen.

Preferable, the present invention is configured so that it can be produced as a single piece using injection molding. Other possible manufacturing processes are stamping, blow molding, or vacuum forming.

It is to be understood that the present invention is not limited to the sole embodiment described above, but encompasses any and all embodiments within the scope of the following claims.

What I claim is:

1. A holder for a slide comprising:

a base, sized to accommodate said slide on a portion of its area and having an integrated hinge that permits a portion of said base to fold over itself and thereby cover said slide;

at least three retaining clips affixed to said base and positioned to contact said slide and hold said slide flush against said base, said at least three retaining clips sized to maintain said portion of said base that covers said slide at a uniform distance from said slide such that said portion of said base is prevented from contacting said slide;

a tab formed as part of said base and flush with the bottom of said base and positioned to permit immobilization of said holder on a horizontal surface; and a clasp positioned on said base to keep said base folded over itself.

2. The holder of claim 1, where said at least three clips comprise:

a first clip positioned at one distal edge of said slide, a second clip positioned at the distal edge opposite said first clip, and a third clip positioned over an identification area of said slide.

3. The holder of claim 1, where said base further comprises retaining posts positioned to maintain said slide in a position underneath said at least three clips.

4. The holder of claim 3, where said retaining posts are sized to maintain the portion of said base that covers said slide at a uniform distance from said slide.

5. The holder of claim 1, further comprising at least one first retaining post positioned to keep said slide positioned underneath said at least three clips and at least two second retaining posts positioned to hold a sampling device against said base.

6. A method of preparing a specimen slide using a slide holder comprising:

a base, sized to accommodate said slide on a portion of its area and having an integrated hinge that permits a portion of said base of fold over itself and thereby cover said slide;

at least three retaining clips affixed to said base and positioned to contact said slide and hold said slide against said base, said at least three retaining clips sized to maintain said portion of said base that covers said slide at a uniform distance from said slide such that said portion of said base is prevented from contacting said slide;

a tab formed as part of said base and flush with the bottom of said base and positioned to permit immobilization of said holder on a horizontal surface; and retaining posts positioned to keep said slide positioned underneath said at least three clips;

a sampling device held in place against said base; and a clasp positioned on said base to keep said base folded over itself; said method comprising the steps of:

removing said sampling device from said base and obtaining a sample on it;

holding said sampling device with said sample in one hand, holding said base in position by pressing on said tab with a finger of the opposite hand;

moving said sampling device to transfer said sample onto said slide;

closing said holder by folding said base along said hinge; and engaging said clasp to keep said holder closed.

7. A holder for a slide comprising:

a base, sized to accommodate said slide on a portion of its area and having an integrated hinge that permits a portion of said base to fold over itself and thereby form a cover over said slide;

at least three retaining clips affixed to said base and positioned to contact said slide and hold said slide flush against said base, said at least three retaining clips sized to maintain said portion of said base that covers said slide at a uniform distance from said slide such that said portion of said base is prevented from contacting said slide;

at least one retaining post positioned to keep said slide positioned underneath said at least three clips;

a tab for handling said holder, said tab formed as part of said base and flush with the bottom of said base and positioned to permit immobilization of said holder on a horizontal surface; and a clasp positioned on said base to keep said cover folded over and covering said slide.

8. The holder of claim 7, where said at least three clips comprise:

a first clip positioned at one distal edge of said slide, a second clip positioned at the distal edge opposite said first clip, and a third clip positioned over an identification area of said slide.

9. The holder of claim 7, where said retaining posts are sized to maintain said cover at a uniform distance from said slide.

10. The holder of claim 1, further comprising at least two second retaining posts positioned to hold a sampling device against said base.

\* \* \* \* \*